United States Patent [19]

Lappe et al.

[11] Patent Number: 5,151,537
[45] Date of Patent: Sep. 29, 1992

[54] PROCESS FOR THE RECOVERY OF RHODIUM FROM THE RESIDUES OF DISTILLATION PROCESSES

[75] Inventors: Peter Lappe, Dinslaken; Helmut Springer, Oberhausen, both of Fed. Rep. of Germany

[73] Assignee: Hoechst Aktiengesellschaft, Fed. Rep. of Germany

[21] Appl. No.: 741,643

[22] Filed: Aug. 7, 1991

[30] Foreign Application Priority Data

Aug. 8, 1990 [DE] Fed. Rep. of Germany ....... 4025074

[51] Int. Cl.$^5$ .................. B01J 31/40; C07C 45/50; C07C 47/02
[52] U.S. Cl. ..................................... 556/136; 556/13
[58] Field of Search ............... 556/13, 136; 546/16; 540/541; 544/47

[56] References Cited

U.S. PATENT DOCUMENTS

| | | | |
|---|---|---|---|
| 4,390,473 | 6/1983 | Cooper | 260/429 R |
| 4,612,402 | 9/1986 | Muccigrosso et al. | 556/136 X |
| 4,904,808 | 2/1990 | Devon et al. | 556/136 X |
| 5,099,047 | 3/1992 | Sato et al. | 556/136 |
| 5,099,048 | 3/1992 | Brookhart et al. | 556/136 |

FOREIGN PATENT DOCUMENTS

| | | |
|---|---|---|
| 15379 | 9/1980 | European Pat. Off. . |
| 322661 | 7/1989 | European Pat. Off. . |
| 348833 | 1/1990 | European Pat. Off. . |
| 424736 | 5/1991 | European Pat. Off. . |

*Primary Examiner*—Arthur G. Prescott
*Attorney, Agent, or Firm*—Jordan B. Bierman

[57] ABSTRACT

The recovery of rhodium, present as a homogeneous dissolved complex compound especially in residues of products of the oxo process, is carried out in a two-stage process. In the first stage, the residues are treated with a gas-containing oxygen in the presence of a $C_2$- to $C_4$-monocarboxylic acid and an alkali metal salt of a $C_2$- to $C_4$-monocarboxylic acid, and are then extracted with water. In the second reaction stage, they are treated again with a gas-containing oxygen, an aldehyde, a $C_2$- to $C_4$-monocarboxylic acid, and an alkali metal salt of a $C_2$ to $C_4$ monocarboxylic acid, and are extracted once more with water.

32 Claims, No Drawings

PROCESS FOR THE RECOVERY OF RHODIUM FROM THE RESIDUES OF DISTILLATION PROCESSES

This Application claims the priority of German Application P 40 25 074.1, filed Aug. 8, 1990.

The present invention relates to an improved process for the recovery of rhodium from residues which are obtained in the distillation of products of reactions catalyzed by rhodium, with special reference to the oxo process.

BACKGROUND OF THE INVENTION

The preparation of aldehydes and alcohols by adding carbon monoxide and hydrogen to olefinic double bonds (hydroformylation) is known. The reaction is catalyzed by metals of Group VIII of the Periodic Table (IUPAC version) or compounds thereof, and forms carbonyls or hydridocarbonyls under the reaction conditions. Formerly, cobalt and cobalt compounds were employed almost exclusively as the catalysts; nowadays rhodium catalysts are used increasingly, even though rhodium is several times more expensive than cobalt. Rhodium is used in this reaction on its own or in combination with complexing agents, for example organic phosphines. Whereas the oxo process using rhodium as catalyst requires reaction pressures of 25 to 30 MPa, pressures of 1 to 5 MPa are sufficient if rhodium complex compounds are employed.

In many cases rhodium catalysts give rise to distinct advantages. They possess a higher activity and selectivity. Furthermore, they enable the manufacturing plant to be operated in many respects free from problems, in particular as to the operation of the synthesis and the discharge of the products from the reactor. Finally, the conventional oxo process based on cobalt catalysts can be switched over in many cases, using the existing pieces of equipment, to rhodium catalysts with only minor capital expenditure.

Considerable difficulties are, however, experienced in achieving the loss-free—or at least approximately loss-free—separation and recovery of the rhodium, irrespective of whether it is employed with or without additional complexing agents. After the conclusion of the reaction, the rhodium is dissolved in the hydroformylation product in the form of the carbonyl compound. It can, in certain cases, also contain further ligands.

The crude oxo product is usually worked up by reducing the pressure in several stages, by initially reducing the synthesis pressure (which is about 1 to 30 MPa, depending on the type of rhodium catalyst employed) to about 0.5 to 2.5 MPa. In the course of this, synthesis gas dissolved in the crude product is set free. It is then possible to reduce the pressure to normal. The removal of the rhodium is carried out either directly from the crude product or from the residue of the distillation of the crude product.

The first route is followed if rhodium without additional complexing agents has been employed as the catalyst in the preceding hydroformylation stage. The second variant is used if the rhodium catalyst also contains, in addition to carbon monoxide, further ligands, such as phosphines or phosphites, in a complex combination. It can also be used if, although the hydroformylation has been carried out using rhodium alone, a complexing agent has been added to the crude product after releasing the pressure in order to stabilize the rhodium. Basically, it must be borne in mind that the noble metal is present in the crude product in a concentration of only a few ppm, and its removal therefore requires a very meticulous operation. In addition, difficulties can arise from the fact that the rhodium sometimes changes into the metallic form, or forms multinuclear carbonyls when the pressure is released, particularly if it has been employed without a ligand. A heterogeneous system composed of the liquid organic phase and the solid phase containing rhodium or rhodium compounds is then formed.

The recovery of rhodium from the products of the oxo process, including the residues of the crude oxo products, has been investigated many times. Research has led to the development of numerous processes, of which a few have also been used on an industrial scale.

The subject of U.S. Pat. No. 4,400,547 is the hydroformylation of olefins having 2 to 20 carbon atoms in the presence of unmodified rhodium as catalyst. After the conclusion of the reaction, a complex-forming compound such as triphenylphosphine is added to the crude oxo product and the aldehyde is distilled off. The distillation residue is then treated with oxygen in order to split the ligands back out of the complex and recover the rhodium in an active form. Separation of the rhodium and the distillation residue is not possible by this procedure.

The removal of noble metals such as rhodium from high-boiling hydroformylation residues is also described in U.S. Pat. No. 3,547,964. For this purpose, the residues are treated with hydrogen peroxide in the presence of acids, such as formic acid, nitric acid, or sulfuric acid. Limits are, however, set to the industrial use of the process on account of the high cost of hydrogen peroxide and the problems associated with its handling.

In accordance with DE 24 48 005 C2, a distillation residue containing rhodium is first treated with acids and peroxides. Excess peroxides are then destroyed by heating, and the aqueous solution containing the catalyst metal is reacted, in the presence of a water-soluble organic solvent, with hydrogen halide acid or alkali metal halides and also with tertiary phosphines and carbon monoxide or compounds which donate carbon monoxide. Once again, this procedure requires the use of peroxides, with the disadvantages described above, and the use of materials of construction stable to halogens.

Finally, EP 15,379 B1 describes a process for regenerating a rhodium catalyst which contains ligands and which has been deactivated in a hydroformylation reaction. This is effected by adding an aldehyde to the catalyst in an amount such that at least 1 mol aldehyde is present per mole of rhodium and per mole of ligand. Oxygen in the form of air is then passed through the mixture of catalyst and aldehyde, the solid oxidized ligand is removed, and the ratio of ligand to rhodium is adjusted to the value desired for the hydroformylation reaction. Although this procedure permits the activity of the catalyst to be restored, it does not make possible either the recovery of the rhodium or the elimination of the impurities which are not oxidized by the action of oxygen or air or which do not give conversion products sparingly soluble or insoluble in the organic medium.

SUMMARY OF THE INVENTION

The object was, therefore, to develop a process which avoids the foregoing disadvantages and which ensures at least a substantially loss-free recovery of the noble metal in the simplest possible manner.

The invention is particularly directed to a process for the recovery of rhodium which is present in a complex combination with an organic phosphorus (III) compound in residues from the distillation of products of the oxo products. The residues are treated with an oxygen-containing gas in an initial reaction stage at 60° to 120° C., under normal or elevated pressure, in the presence of a $C_2$- to $C_4$-monocarboxylic acid and an alkali metal salt of a $C_2$- to $C_4$ monocarboxylic acid. The rhodium is then extracted in the form of a water-soluble compound by means of water, and the aqueous and organic phases are separated from one another. The organic phase is again treated with an oxygen-containing gas under normal or elevated pressure at 60° C. to 120° C. in a second reaction stage in the presence of a $C_2$ to $C_4$-monocarboxylic acid, an alkali metal salt of $C_2$- to $C_4$-monocarboxylic acid, and with the addition of an aldehyde before treatment with oxygen; thereafter removing the rhodium present in the organic phase by extraction with water.

The method according to the invention requires no great expenditure on equipment or chemicals. Nevertheless, it results, surprisingly, in the recovery of over 95% of the rhodium employed. In this procedure, the metal is produced in a form which enables it to be used again as a catalyst without special additional measures.

DETAILED DESCRIPTION OF THE INVENTION

The new process starts from residues of the hydroformylation of olefinically unsaturated compounds which remains in the distillation sump after the aldehydes (and the alcohols formed as byproducts) have been distilled off. They are composed essentially of fairly high molecular weight compounds which have been formed from the aldehydes by an aldol condensation and can also eliminate water in a secondary reaction, with the formation of unsaturated compounds. The nature of the compounds which have been hydroformylated is unimportant for the procedure.

Accordingly, it is possible to employ both residues resulting from the reaction of olefins with carbon monoxide and hydrogen, and also fairly high molecular weight products which are formed when olefinically unsaturated compounds react and which also contain functional groups in the molecule in addition to the double bond. The main purpose of the new process is, however, the recovery of rhodium from residues of the hydroformylation of olefins having 2 to 12 carbon atoms, depending on the economic importance of the aldehydes prepared therefrom.

In addition to the saturated and unsaturated condensation products, the residues can also contain compounds which react with the rhodium ions to form complexes and are, in most cases, present in excess in relation to the rhodium. These include organic phosphorus (III) compounds, in particular phosphines and phosphites, and preferably the aryl derivatives such as triphenylphosphine and triphenyl phosphite. Their function is to improve the selectivity of the reaction by the formation of stable complex compounds during the reaction and, thereafter, to prevent the deposition of metallic rhodium. The ratio of the ligand to rhodium in the reaction mixture is preferably 2 to 150, in particular 5 to 50, mol/mol. Owing to their low volatility, the two components are also present in the distillation residue in approximately the same ratio, the rhodium concentration being between 30 and 1000 ppm by weight, preferably 100 to 500 ppm by weight.

In accordance with the invention, the distillation residue is treated with oxygen in the first reaction stage. The oxidizing agent is employed in pure form or as an oxygen-containing gas mixture such as air. The amount of oxygen can be varied within wide limits. It is preferably based on the concentration of the phosphorus (III) compounds in the residue. It is advisable to use 10 to 2000, in particular 100 to 1200, mols of oxygen per mol of phosphorus (III) compound.

In accordance with the invention, the reaction of the distillation residue (also referred to as untreated residue) with oxygen is carried out in the presence of a saturated, linear or branched monocarboxylic acid having 2 to 4 carbon atoms. Examples of suitable acids are acetic acid, propionic acid, n-butyric acid, and isobutyric acid. Acetic acid and propionic acid have proved particularly suitable. They are employed in the customary commercial form and in an amount such that about 1 to 150, preferably 5 to 50, mols of acid are present per mol of rhodium. The acid is added to the residue before the reaction with oxygen irrespective of whether acid can itself be formed in the course of the reaction owing to the presence of small amounts of aldehyde in the residue. The exact mode of action of the acid is not known. A variety of observations indicate that it acts as an initiator; i.e. it has a decisive influence on the starting of the reaction.

A further and very important characteristic of this stage of the process is the presence of an alkali metal carboxylate in the residue while oxygen is being passed into the mixture of high-boiling compounds. The nature of its intervention in the course of the reaction also cannot be explained clearly. However, it has been found that the addition of the carboxylate results in a marked increase in the amount of rhodium recovered, i.e. a further reduction of the rhodium remaining dissolved in the organic phase.

The alkali metal carboxylates employed for the purposes of the new process are the salts of saturated, linear or branched monocarboxylic acids having 2 to 4 carbon atoms. The sodium and potassium salts of acetic acid, propionic acid, n-butyric acid, and isobutyric acid have proved particularly suitable. They are used in an amount of 10 to 250, preferably 25 to 100, mols of carboxylate per mole of rhodium. The commercially available salts are suitable, but these dissolve only gradually in the course of the oxidation. It is therefore more advantageous to add free acid and an equivalent amount of alkali metal hydroxide to the residue; these dissolve immediately and homogeneously and are thus fully effective.

The reaction of the residue with oxygen is carried out at 60° to 120° C., preferably 80° to 100° C. It can be carried out under normal or elevated pressure, pressures between 0.2 and 1.0 MPa having proved particularly suitable.

In a preferred embodiment of the first stage of the inventive process, the residues on which oxygen acts contain rhodium in a concentration of about 100 ppm by weight or less, preferably 30 to 90 ppm by weight. This is because it has been found that the residual amounts of rhodium in the organic phase after the treatment are particularly low if the metal concentration in the original solution is within the range mentioned. It is therefore advisable to dilute appropriately solutions in which the rhodium concentration is more than about 100 ppm by weight. Suitable diluents are, in particular, fairly high-boiling aliphatic or aromatic hydrocarbons; mixtures of hydrocarbons, such as toluene and xylene; and distillation residues which have been freed from the rhodium catalyst.

The reaction time depends on the concentration of rhodium and ligand in the distillation residue. It is also determined by the amount of oxygen employed and by the reaction temperature and pressure. High concentrations of the dissolved substances require longer treatment times than low concentrations. A large supply of oxygen and increased pressure reduce the reaction time, as does vigorous mixing of the residue with oxygen. Temperatures near the lower and upper regions of the range claimed are somewhat less effective than those in the middle range.

When the treatment with oxygen is concluded, the residue is extracted with water, thereby forming an organic phase and an aqueous phase. This is carried out at temperatures between 20° to 80° C., preferably at 30° to 70° C., in one, or preferably more, stages. The amount of water employed is based on the partition equilibrium between the organic and aqueous phases of the substance to be extracted and the desired concentration of rhodium in the aqueous phase.

As soon as the extraction is complete, the phases are separated from one another and oxygen-containing gas is again allowed to act on the organic phase in the second reaction stage. In this connection, the organic solution containing residual rhodium can be used as is, i.e. just as it is produced after the extraction. Prior drying is not necessary nor is removal of solvent which may have been added to the residue.

The treatment of the organic phase in the second reaction stage differs from the treatment of the residue in the first reaction stage in that an aldehyde is added to the solution containing the rhodium before reaction with oxygen. Aliphatic aldehydes having 2 to 4 carbon atoms in the molecule have proved suitable; acetaldehyde and propionaldehyde are preferred. The amount of aldehyde to be added to the reaction mixture is based on the amount of residue. It has proved suitable to use 0.01 to 2.0 kg of aldehyde per kg of residue; a ratio of 0.05 to 1.0 kg of aldehyde per kg of residue is preferred. It is not necessary, of course, to use the aldehydes in the form of the pure compounds. It is also possible to use, with equally good results, mixtures of aldehydes, for example mixtures of structural isomers of aldehydes or of aldehydes of different molecular weights.

In addition to an aldehyde, a saturated, linear or branched monocarboxylic acid having 2 to 4 carbon atoms and the alkali metal salt of such a carboxylic acid are added to the reaction mixture, as in the first stage. It is not necessary for the carboxylic acid and the salt to be the same in the two reaction stages; on the contrary, it is also possible to use different acids and/or salts in the two stages. However, it is once again advantageous to prepare the carboxylate directly in the organic solution from acid and the equivalent amount of alkali metal hydroxide to ensure that it is dissolved immediately and homogeneously.

In principle it is possible to use the same rhodium/carboxylic acid and/or rhodium/carboxylate ratio in the second reaction stage as in the first stage, i.e. to use 1 to 150, preferably 5 to 50, mols of acid and 10 to 250, preferably 25 to 100, mols of carboxylate per mol of rhodium. However, it has proved preferable to use the same absolute amount of carboxylic acid and/or carboxylate in the second stage. If it is borne in mind that, after the first reaction stage, the distillation residue contains only about one tenth of the amount of rhodium originally present, the excess of carboxylic acid and/or carboxylate resulting in the second stage will be ten times higher than that in the first stage. Thus 10 to 1500 mol of acid and 100 to 2500 mol of salt should be used per mol of rhodium.

Pure oxygen or oxygen diluted with inert gases is passed through the solution, which may also contain a solvent, in a large excess over the dissolved rhodium compound present. The conditions under which the treatment with oxygen is carried out are the same as those in the first stage. The reaction is carried out at 60° to 120° C., preferably 80° to 100° C., at normal or elevated pressure. Pressures between 0.2 and 1.0 MPa have proved particularly suitable.

Apart from the rhodium concentration, the reaction time depends, as in the first stage, essentially on the pressure, temperature, and the supply of oxygen; i.e. the absolute amount of oxygen and the distribution of the oxygen in the liquid phase. Also, the effects of altering these parameters are the same for the second stage as for the first stage.

When the treatment with oxygen is concluded, the residue is again extracted with water. This part of the second reaction stage is also carried out as described for the first stage. It is preferable to extract with the rhodium salt solution obtained in the first reaction stage. In addition, it is possible to use this solution repeatedly for the extraction, in order to achieve an enrichment of the metal in the solution. The aqueous solution can be used for the preparation of catalyst directly, i.e. without additional purification.

The reaction of the distillation residue can be carried out continuously or batchwise in conventional equipment. The oxygen or the gas-containing oxygen is passed into the reactor via distribution devices, and the uniform mixing of the liquid and gaseous phases is assisted, if necessary, by stirring.

The new process makes it possible to recover more than 95% of the rhodium present in the distillation residues of the products of hydroformylation. The procedure according to the invention acquires particular significance from the fact that it can be applied quite generally to the products of reactions which take place under the catalytic influence of homogeneously dissolved rhodium compounds. It was not to be expected that the combination of the two different reaction stages, each of which is in itself suitable for separating rhodium compounds, even if incompletely, from organic solutions, would lead to better results than the repeated use of each of the two stages.

The following examples illustrate the invention; however, they are, of course, not intended to limit it.

In Table 1 the feed stocks are characterized by their essential distinguishing values.

Examples 1, 4, 5 and 8 represent the two-stage process according to the invention. This process is compared in Examples 2 and 7 with a procedure which corresponds to the second stage of the new process, and is compared in Examples 3 and 6 with a process in which the first stage of the process of the invention is used twice successively.

TABLE 1

| Feed stocks | Material A | Material B |
|---|---|---|
| Rh content (ppm) | 196 | 436 |
| P (III) (mmol/kg) | 30 | 33 |
| P tot. (mmol/kg) | 31.7 | 54.8 |

Material A: Distillation residue from the hydroformylation of ethylene at 130 to 180° C. and 20 to 30 MPa.
Material B: Distillation residue from the hydroformylation of propylene at 130 to 180° C. and 20 to 30 MPa.

EXAMPLE 1

Invention 214.3 g of distillation residue A (Rh content: 42 mg), 385.7 g of xylene, 8.2 g of 30% sodium hydroxide solution, and 5.1 g of 99.5% propionic acid are placed in a 1 liter glass autoclave provided with jacket heating, and are heated to 80° C. with stirring in the course of 15 minutes. 45 liters per hour of air are then passed in through a dip pipe under a pressure of 0.35 MPa for 3 hours. The reaction is carried out at a constant internal pressure of 0.35 MPa and a constant temperature of 80° C. The exit gas is released via a needle valve in the lid of the autoclave and is passed into a flask equipped with a condenser.

When the reaction is complete, the contents of the autoclave are cooled to 60° C. in the course of about 15 minutes and the introduction of air is stopped. The pressure is then released, 200 g of water are added to the reaction mixture and the latter is stirred at 50° to 60° C. for a further 15 minutes. The product is removed from the reactor, the phases are separated, and the organic phase is extracted twice with 200.0 g of water each time. After the treatment, the organic phase still contains 2.8 mg of Rh, corresponding to 6.6% of the Rh present in the feed stock.

50 g of propionaldehyde, 8.2 g of 30% sodium hydroxide solution, and 5.1 g of 99.5% propionic acid are added to the organic phase (563.7 g), and the mixture is treated with air as in the first stage. After being extracted three times with water as in stage 1, the organic phase contains 0.3 mg of Rh, corresponding to 0.7% of the Rh present in the feed stock.

EXAMPLE 2

Comparison 214.3 g of distillation residue A, 335.7 g of xylene, 8.2 g of 30% sodium hydroxide solution, 5.1 g of 99.5% propionic acid, and 50 g of propionaldehyde are initially subjected to oxidation under the same conditions and in the same manner as Example 1. After the treatment, the organic phase still contains 2.5 mg of Rh, corresponding to 6.0% of the metal present in the feed stock.

EXAMPLE 3

Comparison

The equivalent amounts of distillation residue, xylene, sodium hydroxide solution, and propionic acid are employed as in Example 1. After the two-stage treatment—without adding propionaldehyde in the second stage—and extraction, the organic phase still contains 2.7 mg of Rh, corresponding to 6.4% of the metal present in the feed stock.

EXAMPLE 4

Invention 260.7 g of distillation residue A, 339.3 g of xylene, 8.2 g of 30% sodium hydroxide solution, and 5.1 g of 99.5% propionic acid are placed in a 1 liter glass autoclave provided with jacket heating, and are heated to 80° C. with stirring in the course of 15 minutes. 45 liter per hour of air are then passed in through a dip pipe under a pressure of 0.33 MPa for a period of 3 hours. The reaction is carried out at a constant internal pressure of 0.35 MPa and a constant temperature of 80° C. The exit gas is released via a needle value in the lid of the autoclave and is passed into a flask equipped with a condenser.

When the reaction is complete, the contents of the autoclave are cooled to 60° C. over about 15 minutes and the introduction of air is stopped. The pressure is then released, 200.0 g of water are added to the reaction mixture, and the latter is stirred at 50° to 60° C. for a further 15 minutes. The product is removed from the reactor, the phases are separated, and the organic phase is extracted twice with 200.0 g of water each time. After the treatment, the organic phase still contains 4.0 mg of Rh, corresponding to 7.8% of the metal present in the feed stock.

50 g of propionaldehyde, 8.2 g of 30% sodium hydroxide solution, and 5.1 g of 99.5% propionic acid are added to the organic phase (543.7 g), and the mixture is treated with air as in the first stage. After being extracted with water three times as in stage 1, the organic phase contains 1.2 mg of Rh, corresponding to 2.3% of the metal present in the feed stock.

EXAMPLE 5

Invention 96.3 g of distillation residue B, 503.7 g of xylene, 8.2 g of 30% sodium hydroxide solution, and 5.1 g of 99.5% propionic acid, in a manner analogous to that of Example 1, are initially reacted at a temperature of 80° C., a pressure of 0.35 MPa, and an air rate of 47.7 liters/hour for a period of 6 hours. When the reaction is complete, the solution is treated as in Example 1; the organic phase contains 9.5 mg of Rh, corresponding to 22.6% of the metal present in the feed stock.

50 g of propionaldehyde, 8.2 g of 30% sodium hydroxide solution, and 5.1 g of 99.5% propionic acid are added to the organic phase (573.7 g), and the mixture is treated with air as in the first stage (reaction time: 4 hours). After being extracted three times with water as in the first stage, the organic phase contains 2.0 mg of Rh, corresponding to 4.8% of the metal present in the feed stock.

EXAMPLE 6

Comparison 96.3 g of distillation residue B, 503.7 g of xylene, 8.2 g of 30% sodium hydroxide solution, and 5.1 g of 99.5% propionic acid, as in Example 1, are initially reacted at a temperature of 80° C., a pressure of 0.35 MPa, and an air rate of 47.7 liters/hour for a period of 6 hours. When the reaction is complete, the solution is treated as in Example 1; the organic phase contains a 9.5 mg of Rh, corresponding to 22.6% of the metal present in the feed stock.

8.2 g of 30% sodium hydroxide solution and 5.1 g of 99.5% propionic acid are added to the organic phase (537.7 g); that is to say, no propionaldehyde is added, and the mixture is treated as in the first stage (reaction time: 4 hours). After it has been extracted 3 times with water, the organic phase still contains 7.3 mg of Rh, corresponding to 17.4% of the metal present in the feed stock.

EXAMPLE 7

Comparison 96.3 g of distillation residue B, 453.7 g of xylene, 8.2 g of 30% sodium hydroxide solution, 5.1 g of 99.5% propionic acid, and 50.0 g of propionaldehyde, as in Example 3, are initially treated with air under the conditions of Example 5. After extraction as in Example 1, the organic phase still contains 4.7 mg of Rh, corresponding to 11.2% of the metal present in the feed stock.

EXAMPLE 8

Invention 70.0 g of distillation residue B, 530.0 g of xylene, 8.2 g of 30% sodium hydroxide solution, and 5.1 g of 99.5% propionic acid, as in Example 1, are initially reacted at a temperature of 80° C., a pressure of 0.35 MPa, and an air rate of 47.7 liters/hour for a period of 6 hours. When the reaction is complete, the mixture is treated similarly to Example 1; the organic phase contains 6.3 mg of Rh, corresponding to 20.6% of the metal present in the feed stock.

50 g of propionaldehyde, 8.2 g of 30% sodium hydroxide solution, and 5.1 g of 99.5% propionic acid are added to the organic phase (581.2 g), and the mixture is treated as in the first stage (reaction time: 4 hours). After extraction three times with water, the organic phase contains 1.2 mg of Rh, corresponding to 3.9% of the metal present in the feed stock.

While only a limited number of specific embodiments of the invention have been expressly disclosed it is, nonetheless, to be broadly construed and not to be limited except by the character of the claims appended hereto.

What we claim is:

1. A method for the recovery of rhodium present as homogeneously dissolved compounds from a residue of a reaction catalyzed by said rhodium, said method comprising
    treatment of said residue with a first oxygen-containing gas in an initial reaction stage at an initial stage temperature of 60° to 120° C. under an initial stage pressure of at least one atmosphere in the presence of a first monocarboxylic acid having 2 to 4 carbon atoms and a first alkali metal salt of a second carboxylic acid having 2 to 4 carbon atoms;
    a first extraction of said rhodium as a water soluble compound from said residue with water to form an aqueous phase and an organic phase, separating said organic phase from said aqueous phase;
    introducing an aldehyde into said organic phase in a second stage before oxidation with a second oxygen-containing gas at a second stage temperature of 60° to 120° C. under a second stage pressure of at least one atmosphere, a third monocarboxylic acid having 2 to 4 carbon atoms, and a second alkali metal salt of a fourth monocarboxylic acid having 2 to 4 carbon atoms; and
    a second extraction of said rhodium from said organic phase with a water-containing substance.

2. The method of claim 1 wherein said rhodium is in a complex ligand with an organic phosphorous (III) compound in said residue from distillation of products of the oxo process.

3. The method of claim 1 wherein said residue is from hydroformylation of olefins.

4. The method of claim 3 wherein said olefins have 2 to 12 carbon atoms.

5. The method of claim 2 wherein said compound is selected from the group consisting of triphenyl phosphine and triphenyl phosphite.

6. The method of claim 2 wherein a molar ratio of said ligand to said rhodium is 2 to 150.

7. The method of claim 1 wherein there are 30 to 1000 ppm by weight of said rhodium in said residue.

8. The method of claim 1 wherein there are 10 to 2000 mols of oxygen per mol of said phosphorous (III) ligand.

9. The method of claim 1 wherein at least one said first, said second, said third, and said fourth monocarboxylic acid is selected from the group consisting of acetic, propionic, n-butyric, and i-butyric.

10. The method of claim 1 wherein there are 1 to 150 mols of said first monocarboxylic acid per mol of rhodium.

11. The method of claim 1 wherein at least one of said initial stage pressure and said second stage pressure is 0.2 to 1.0 MPa, and said initial stage temperature and said second stage temperature are 80° to 100° C.

12. The method of claim 1 wherein at least one of said first and alkali metal salt and said second alkali metal salt is selected from the group consisting of sodium acetate, potassium acetate, sodium propionate, potassium propionate, sodium n-butyrate, potassium n-butyrate, sodium i-butyrate, and potassium i-butyrate.

13. The method of claim 1 wherein said first alkali metal salt is present in an amount of 10 to 250 mols per mol of rhodium.

14. The method of claim 1 wherein said oxygen-containing gas is air.

15. The method of claim 1 wherein said residue contains not more than 100 ppm of rhodium.

16. The method of claim 1 wherein at least one of said first extraction and said second extraction is carried out at an extraction temperature of 20° to 80° C.

17. The method of claim 1 wherein said aldehyde is selected from the group consisting of acetaldehyde and propionaldehyde.

18. The method of claim 1 wherein said aldehyde is present in a concentration of 0.01 to 2.0 parts by weight per part of said residue.

19. The method of claim 1 wherein said first alkali metal salt and said second alkali metal salt are different, and said first monocarboxylic acid and said second monocarboxylic acid are different.

20. The method of claim 1 wherein at least one of said first salt and said second salt is formed in situ by reaction of said second acid or said fourth acid with at least one alkali metal hydroxide.

21. The method of claim 1 wherein there are 10 to 1500 mols of said third acid per mol of rhodium in said organic phase.

22. The method of claim 21 wherein there are 100 to 2500 mols of said second salt per mol of rhodium in said organic phase.

23. The method of claim 1 wherein said substance is used to extract said rhodium in a subsequent second extraction.

24. The method of claim 1 wherein said substance is recycled to said reaction catalyzed by said rhodium.

25. The method of claim 6 wherein said molar ratio is 5 to 50.

26. The method of claim 7 wherein there are 100 to 500 ppm by weight of said rhodium in said residue.

27. The method of claim 9 wherein there are 100 to 1200 mols of oxygen per mol of said phosphorous (III) ligand.

28. The method of claim 10 wherein there are 5 to 50 mols of said first monocarboxylic acid per mol of rhodium.

29. The method of claim 13 wherein said amount is 25 to 100 mol of said first salt per mol of rhodium.

30. The method of claim 15 wherein said residue contains 30 to 90 ppm of rhodium.

31. The method of claim 16 wherein said extraction temperature is 30° to 70° C.

32. The method of claim 18 wherein said concentration is 0.05 to 1.0 parts by weight per part of said residue.

* * * * *